(12) United States Patent
Peyman

(10) Patent No.: US 6,442,409 B1
(45) Date of Patent: Aug. 27, 2002

(54) DIAGNOSTIC SYSTEM AND METHOD USING RADIANT ENERGY AND IMPLANTS

(76) Inventor: Gholam A. Peyman, 8654 Pontchartrain Blvd., Unit 1, New Orleans, LA (US) 70124

( * ) Notice: Subject to any disclaimer, the term of this patent is extended or adjusted under 35 U.S.C. 154(b) by 0 days.

(21) Appl. No.: 09/532,957

(22) Filed: Mar. 22, 2000

(51) Int. Cl.[7] .................................................. A61B 6/00
(52) U.S. Cl. ...................... 600/318; 600/316; 600/319; 600/407; 600/473; 600/476; 128/899
(58) Field of Search .......................... 600/310, 318–320, 600/407, 316, 473, 476, 558; 128/899

(56) References Cited

U.S. PATENT DOCUMENTS

| | | | |
|---|---|---|---|
| 3,958,560 A | | 5/1976 | March |
| 3,963,019 A | | 6/1976 | Quandt |
| 4,014,321 A | | 3/1977 | March |
| 4,878,910 A | * | 11/1989 | Koziol et al. |
| 4,949,350 A | | 8/1990 | Jewell et al. ................. 372/45 |
| 5,560,356 A | | 10/1996 | Peyman |
| 5,570,697 A | * | 11/1996 | Walker et al. ............... 600/532 |
| 5,754,578 A | | 5/1998 | Jayaraman .................... 372/50 |
| 5,933,444 A | | 8/1999 | Molva et al. .................. 372/75 |
| 6,253,097 B1 | * | 6/2001 | Aronow et al. ............. 600/310 |

* cited by examiner

*Primary Examiner*—Ruth S. Smith
(74) *Attorney, Agent, or Firm*—Alfred N. Goodman; Jeffrey J. Howell

(57) ABSTRACT

A system for testing for the existence of a biomedical condition of an animal test subject having first and second devices for projecting radiant energy. The first device for projecting radiant energy projects a beam of radiant energy into and through the tissue of a portion of the animal test subject. The second device for projecting radiant energy is implanted in the body of the animal test subject and projects a second beam of radiant energy out of the body in response to the projected radiation of the first radiant energy source. The second device for projecting radiant energy can be a mirror that reflects the first beam of radiant energy or it can be a source of radiant energy, such as a vertical-cavity surface-emitting laser, that emits a specific wavelength of light when activated by the first device for projecting radiant energy. A detector positioned outside the body and relative to the second device for projecting radiant energy detects the second beam of radiant energy. A processor in communication with the detector then compiles the information from the detector and calculates changes in the known wavelength of light after passage through the body of the animal test subject, thereby determining the existence of a biomedical condition.

33 Claims, 2 Drawing Sheets

DIAGNOSTIC SYSTEM AND METHOD USING RADIANT ENERGY AND IMPLANTS

FIELD OF THE INVENTION

The present invention relates generally to devices and methods for testing an animal for the existence of a biomedical condition and more particularly to a system for testing an animal for the existence of a biomedical condition, such as hyperglycemia, hypoglycemia or other disorders in the body, using radiant energy either emitted by an implanted vertical-cavity surface-emitting laser or reflected by a mirror.

BACKGROUND OF THE INVENTION

Many medical diagnostic techniques project radiant energy into the body of an animal for testing for the existence of a biomedical condition. For example, the integrity of the skeletal structure may be examined by passing X-rays through the body. The dense bony material substantially blocks the passage of the X-rays, permitting a doctor or other medical care provider to visually inspect for fractures or other defects in the skeletal structure.

X-rays are also used in mammography to detect tumors in the breast. In this technique, the X-rays are passed through the breast such that they do not travel through any bony structure. The X-rays are hindered by tumors in the breast which show up as dark spots on the X-ray film. Although under this technique tumors may be detected earlier than by physical examination, the technique is difficult to administer due to the angle that the X-rays must be passed through the breast.

To examine the soft tissue of the body, other techniques are available. These include, among others, CAT scans and magnetic resonance imaging. Both project radiant energy onto the body for obtaining information about the physical structure of the body. Although these techniques are highly accurate and provide detailed information, they are time consuming to administer and costly to perform.

Further, measurement of the level of certain chemicals or compositions within the body is a diagnostic test of particular interest. Radiant energy may be used in these applications as passage of the radiant energy through particular chemicals or compositions often alters the radiant energy in a manner that can be measured and analyzed. For example, the monitoring of the glucose level of the blood is of particular importance to diabetics. One method of measuring the person's glucose level involves projecting polarized radiation into the body and measuring the optical rotation of the radiation that passes through the body. This optical rotation corresponds to the concentration of the glucose within the body. To be effective, however, the radiation must be passed through a relatively thin area of the body. Thus, the technique is usually performed on a person's earlobes or fingers. However, the skin and other tissue through which the radiant energy passes can interfere with the accuracy of the test.

To overcome the inaccuracies associated with passing the radiant energy through the tissue, attempts have been made to project the radiant energy through the cornea and aqueous humor of the eye. This is done because the concentration of glucose, oxygen and other chemicals in the cornea and aqueous humor, for example, reflects the concentration generally throughout the body. However, several problems are associated with this technique as well. For example, in Quandt U.S. Pat. No. 3,963,019, radiant energy is projected into the eye and reflected off the iris. The reflected radiation is detected and the optical rotation caused by passage of the reflected radiation through the cornea and aqueous humor is determined. However, this method suffers from poor sensitivity, in part because it relies on reflecting the radiant energy off the iris. Other attempts, as shown in March U.S. Pat. No. 3,958,560 and March U.S. Pat. No. 4,014,321, project the radiant energy at a shallow angle into the cornea on one side of the eye, through the aqueous humor, and out the cornea on the opposing side of the eye. Although this test achieves high accuracy, it is difficult to administer because of the shallow angle at which the radiant energy must be passed through the eye. Furthermore, as shown in Peyman U.S. Pat. No. 5,560,356, the disclosure of which is herein incorporated by reference, radiant energy is reflected on a mirror implanted in the eye. This test is also relatively accurate, however, the beam of radiant energy must pass through the aqueous humor and/or cornea of the eye twice, once traveling through the aqueous humor and then reflected off the mirror and again through the aqueous humor out of the eye, each step, including the reflective step, deteriorating the beam of radiant energy and making measurement less accurate.

Thus, there has been a continuing need for a device and method for reliably and easily performing tests using radiant energy for detecting the existence of biomedical conditions. More particularly, there has been a continuing need for a device and method for reliably and easily measuring the level of a substance in the body using radiant energy.

SUMMARY OF THE INVENTION

Accordingly, it is an object of the present invention to provide a system for use in testing for the existence of a biomedical condition using radiant energy that passes through the aqueous humor in the eye once, thereby resulting in a highly accurate measurement device.

Another object of the present invention is to provide a system for use in testing for the existence of a biomedical condition using radiant energy that is easily administered without compromising accuracy.

Still another object of the present invention is to provide a system for use in testing for the existence of a biomedical condition using radiant energy that utilizes a known focused wavelength of light emitted from within the body of a test subject, resulting in a highly sensitive and accurate measurement device.

Yet another object of the present invention is to provide a system for use in testing for the existence of a biomedical condition using radiant energy that repolarizes a light beam as it is reflected off a mirror.

The foregoing objects are basically obtained by providing a system for testing for the existence of a biomedical condition using radiant energy, the combination comprising a radiant energy source for projecting radiation into and through the tissue of a portion of an animal test subject, a light emitter for implantation in the body of the animal test subject for emitting a known wavelength of light through the body when activated by the projected radiation of the radiant energy source, a receiver including a detector positionable relative to the light emitter for detecting the known wavelength of light, and a processor in communication with the detector for calculating changes in the known wavelength of light after passage through the body of the animal test subject to determine the existence of a biomedical condition.

The foregoing objects are also obtained by providing a system for testing for the existence of a biomedical condition using radiant energy, the combination comprising an intraocular lens system having a lens portion and haptics for implantation in an eye of an animal test subject, a radiant energy source for projecting radiation into and through the cornea of the eye of the animal test subject, a reflective device configured and sized for implantation in the body of the animal test subject for reflecting the radiation out of the eye, a receiver including a detector for detecting the reflected radiation, and a processor in communication with the detector for calculating changes in the reflected radiation after passage through the body of the animal test subject to determine the existence of a biomedical condition.

BRIEF DESCRIPTION OF THE DRAWINGS

Referring to the drawings which form a part of this disclosure.

DETAILED DESCRIPTION OF THE INVENTION

Figure 1:
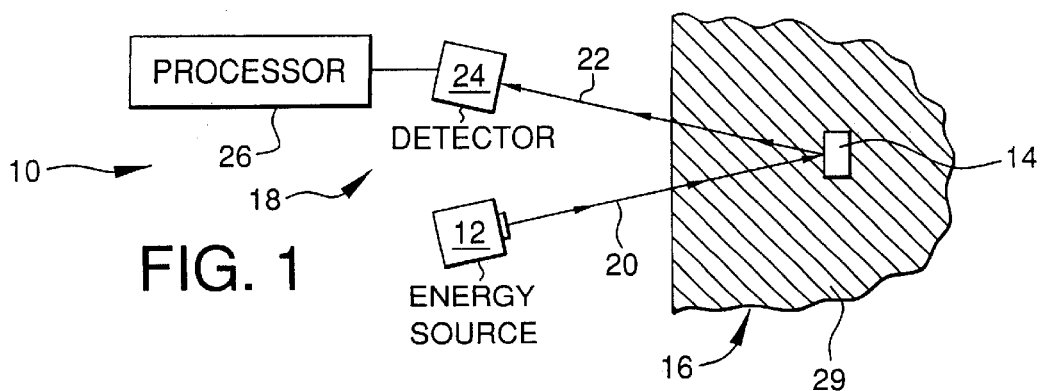
FIG. 1 is a cross-sectional side view of a diagnostic system using implants for emitting radiant energy out of the body in accordance with the present invention.

Referring initially to FIG. 1, a diagnostic system 10 in accordance with the present invention comprises a first radiant energy source 12, a light emitter or second radiant energy source 14 that is implanted within the body 16 of an animal test subject, and a receiver system 18. First radiant energy source 12 is positioned relative to the light emitter 14 to project a first beam of radiant energy or activating beam 20 into the body 16 of the animal test subject and onto the light emitter 14, activating the light emitter. Upon activation, the light emitter emits a second beam of radiant energy or measuring beam 22 that is of a known wavelength back through body 16, which is received by receiver system 18. The receiver system comprises a detector 24 and a processor 26. Detector 24 is positioned to detect the second beam of radiant energy 22, which is processed by processor 26 to provide information regarding changes in the second beam of radiant energy 22 as a result of passing through body 16. This information may then be displayed or further processed to generate information for a doctor or other medical care provider regarding the biomedical condition for which the test is being administered.

First radiant energy source 12 may be any suitable device, such as a laser, capable of producing radiant energy for diagnostic testing. Advantageously, the first beam of radiant energy 20 is any conventional type of light beam that can pass through the tissue of the test subject and then activate light emitter 14. Preferably this type of radiant energy is visible light, blue light or infrared light, or any combination thereof. Each type of light is generally better suited to activate a specific light emitter. For example, when measuring glucose, preferably an infrared light is directed toward the eye, the infrared light activates a specific light emitter having a specific wavelength best suited for measuring glucose, such as red light.

Light emitter 14 is preferably a vertical-cavity surface-emitting laser (VCSEL). However, light emitter 14 can be any type of device that is activated by an external radiant energy source, thereby emitting a known wavelength of light. Conventional VCSELs are semiconductor lasers having a semiconductive layer of optically active material, such as gallium arsenide or indium phosphide, sandwiched between mirrors formed of highly reflective layers or stacks of metallic material, such as aluminum arsenide, gallium arsenide or aluminum gallium arsenide or some combination thereof. Generally, one of the mirror stacks is partially reflective so as to pass a portion of the coherent light that builds up in a resonating cavity formed by the layer of optically active material. For further background information pertaining to VCSELs, see U.S. Pat. No. 5,933,444 to Molva et al.; U.S. Pat. No. 5,754,578 to Jayaraman; and U.S. Pat. No. 4,949,350 to Jewell et al., the disclosures of which are herein incorporated by reference.

Figure 2:
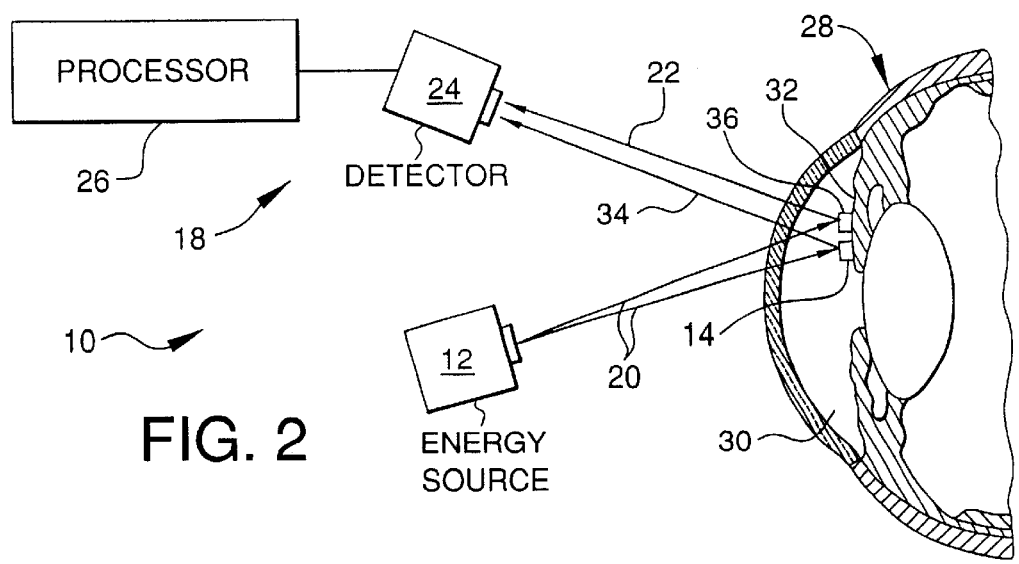
FIG. 2 is a cross-sectional side view of the diagnostic system of FIG. 1 illustrating ocular implants attached to the iris of an eye.
Figure 3:
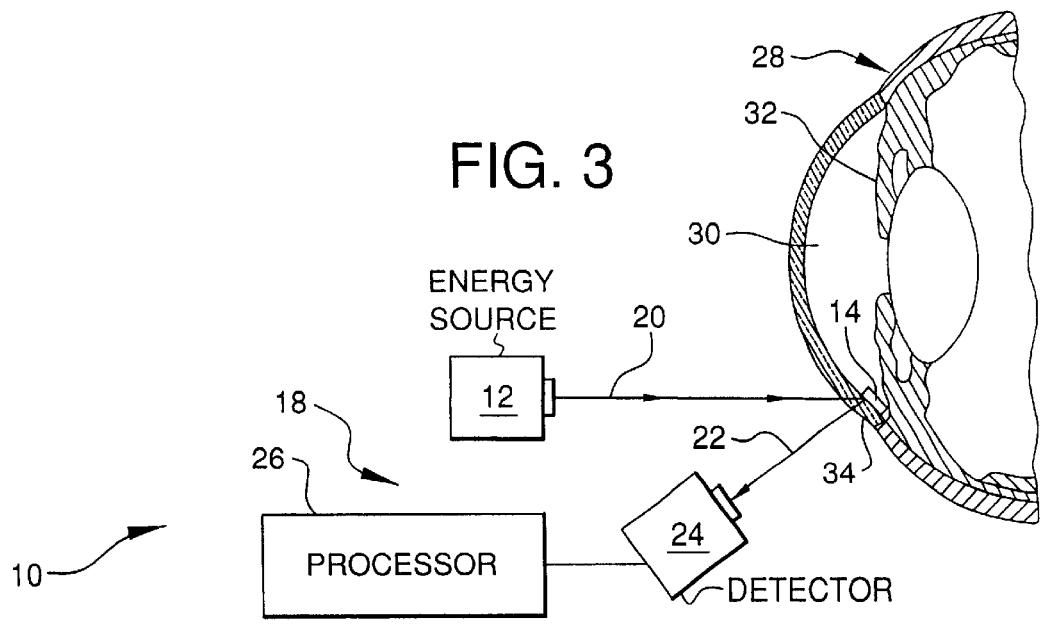
FIG. 3 is a cross-sectional side view of the diagnostic system of FIG. 1 illustrating an ocular implant attached to the corneal stroma of an eye.

Preferably, light emitter 14 is implanted in the eye 28, as shown in FIGS. 2 and 3; however, it my be implanted in tissue 29 of a leg, torso, arm, or any other suitable location, as seen if FIG. 1. By implanting light emitter in the eye 28, it is possible to obtain more accurate results than if the radiant energy is passed through other tissue or skin in the body. The VCSELs may be placed anywhere in the anterior chamber 30 of the eye 28, such on the iris 32, as shown in FIG. 2, or on the corneal stroma 34, as shown in FIG. 3.

Furthermore, it is possible to implant one, two or more light emitters or VCSELs in the anterior chamber of the eye. As seen in FIG. 2, two sources of radiant energy 14 and 36 are implanted on the iris 32, this is not meant to limit the present invention to only two sources of radiant energy, but is shown merely as an example. The present invention may have any number of light emitters or VCSELs implanted anywhere in the anterior chamber of the eye and/or in the body.

When a plurality of VCSELs are implanted in the eye, each source emits a beam of radiant energy 22 and 34, directed out of the eye and towards the receiver system 18. Since the beams of radiant energy 22 and 34 originate from within the eye, the beams only pass through the aqueous humor once, reducing the modulation or deterioration of the light and making the resultant measurement highly accurate. By implanting a plurality of VCSELs in the body or the eye, each VCSEL having a different active layer designed to produce different known wavelengths of light, allows the diagnostic testing of more than one biological condition at one time with one activating beam of radiant energy from the first radiant energy source.

The receiver system 18 is preferably a spectroscopy or a polarization analyzer, but may be any system capable of detecting and processing the second beam of radiant energy 22 for a biological condition. Receiver system 18 is comprised of detector 24 positioned to detect the second beam of radiant energy 22 and processor 26.

Detector 24 can be any suitable detector that is capable of detecting the light emitted from the eye.

Processor 26 processes the detected signal to determine the absorption or fluorescence of each known wavelength of light in the detected signal. Each substance in the body absorbs a certain amount of energy from light of a specific wavelength. When it is known what substance is to be measured, the specific wavelength can be determined and the VCSEL having that specific wavelength can be activated by a preselected first source of radiant energy. As the light exits the eye through the aqueous humor in the anterior chamber, a certain amount of light will be modulated or absorbed by the substance, which is measured in the receiver system. From this measurement, the amount of the substance in the body can be determined. It is also possible to measure the fluorescence of the emitted light. Each substance in the body causes a certain wavelength to fluoresce a certain amount, allowing the substance to be measured depending on how much the specific wavelength of light fluoresces.

Specially developed software relying on chemometrics may be used in processor 26 to determine the concentration of various compounds based upon the strength of the wavelengths received by detector 24. Under this method, samples having a range of known compositions are presented to diagnostic system 10 prior to use for correlation by the software in processor 26. From the baseline information, the software generates algorithms for calculating the composition or concentration information from the detected signals during actual use.

Operation

As seen in FIGS. 2 and 3, at least one light emitter or VCSEL 14 is implanted into the anterior chamber 30 of the eye 28, preferably either on the iris 32 or on the corneal stroma 34. First radiant energy source 12, preferably a laser capable of emitting blue light, infrared light or visible light is then positioned and aimed at a VCSEL. The first radiant energy source externally pumps the VCSEL and excites the active layer of material. When the layers of optically active material sandwiched between the mirrors are pumped externally by first radiant energy source 12, the active layers lase. This lasing causes a coherent light build up in the resonating cavity, thus emitting a focused specific or known wavelength of light. When multiple VCSELs having different compositions of layers of optically active material are implanted in the eye, a particular desired wavelength can be emitted out of the eye by determining which VCSEL is to be activated and choosing the correct radiant energy to active that particular VCSEL.

By predetermining the optically active material in the VCSEL and the proper radiant energy from first radiant energy source 12, a particular biomedical condition may be detected. The specific wavelength of light from the light emitter or measuring beam 22 is altered by passage through certain chemicals or compositions in a manner that can be detected and processed such that the concentration of the chemical or composition may be determined. The types of compositions or compounds that may be detected by the present invention include glucose, antibiotics, anti-inflammatory agents, hormones, anti-fungals, proteins and lystokines (a type of hormone). This list is not exclusive and other compounds or compositions, the presence and concentration of which may be readily determined by use of the present invention, will be readily apparent to those skilled in the art.

Figure 4:
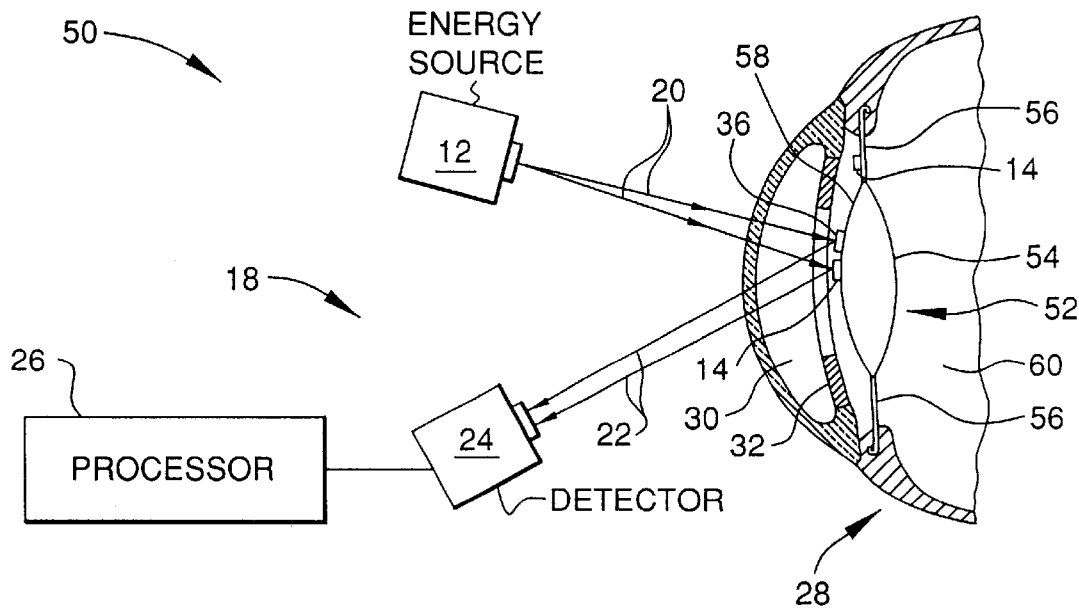
FIG. 4 is a cross-sectional side view according to a second embodiment of the present invention in which the ocular implants are attached to an intraocular lens system.

Second Embodiment of FIG. 4

Referring to FIG. 4, according to a second embodiment of the present invention, diagnostic system 50 has a first radiant energy source 12, a light emitter 14, and a receiver system 18. The light emitter is attached to an intraocular lens system 52 having a lens portion 54 and haptics 56 and is implanted in the eye 28. As described above, light emitter 22 is preferably a VCSEL and as will be readily apparent to one skilled in the art, multiple VCSELs may be attached simultaneously in any number of locations on the intraocular lens system. However, light emitter 14 can be any type of device that is activated by an external radiant energy source, thereby emitting a known wavelength of light. A light emitter 14 may be attached to surface 58 of lens portion 54, embedded into lens portion 54 or attached to the haptics 56 or any combination thereof. Intraocular lens system 52 may replace the natural lens, as shown in FIG. 4, or be added in addition to the natural lens, and it may be placed in the anterior chamber 30 or in the posterior chamber 60 of the eye 28. For a further description of intraocular lens systems see U.S. Pat. Nos. 4,581,031 and 4,666,446, both to Koziol et al, which are herein incorporated by reference.

The use and operation of diagnostic system 50 is substantially similar to diagnostic system 10 and the features of diagnostic system 50, which are similar to diagnostic system 10, are identified with like reference numbers. The same description of those similar features is applicable.

Figure 5:
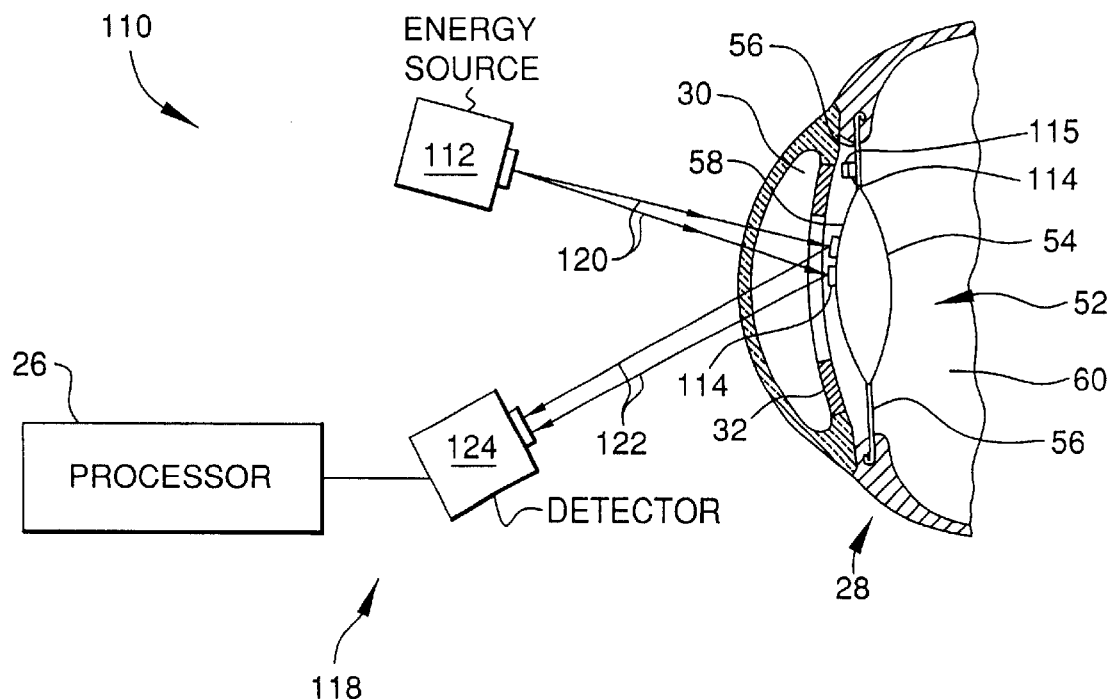
FIG. 5 is a cross-sectional side view according to a third embodiment of the present invention in which reflective devices are attached to an intraocular lens for reflecting radiant energy out of the eye.

Third Embodiment of FIG. 5

Referring to FIG. 5, a third embodiment of the present invention comprises diagnostic system 110 which has a radiant energy source 112, a mirror 114, and a receiver system 118. The mirror is attached to or formed with an intraocular lens system 52 substantially similar to the intraocular lens system described above.

Radiant energy source 112 may be any suitable device capable of producing a beam of radiant energy 120 for use in diagnostic testing. Advantageously, the radiant energy beam is any conventional type of light beam that can be passed through the body of the test subject and is altered by the passage through the body such that a particular biomedical condition may be detected. For example, many types of radiant energy satisfy this criteria, such as polarized radiant energy, near-infrared radiant energy, or conventional laser light.

Additionally, when it is desired to project a beam of a specific wavelength, beam of radiation 120 may be generated by an acousto-optic tunable filter (AOTF), solid-state wavelength-tuning device. An AOTF is an optical crystal, such as one specially prepared from quartz or tellurium oxide, having a high frequency transducer attached to one side. The transducer produces a radio frequency, which interacts with light waves passed through the crystal such that the crystal acts as a narrow-line band-pass filter. Accordingly, at any given applied radio frequency, the AOTF transmits only a single wavelength of light. By quickly tuning the radio source to different frequencies, radiation having a number of precisely known wavelengths is generated.

Reflective device 114, which is implanted in the eye 28 of a patient, is positioned within the eye 28 to reflect outwardly the beam of radiation 120. Reflective device 114 may be coupled to, attached to or formed with surface 56 of lens portion 54, embedded into lens portion 54 or attached to the haptics 56 or any combination thereof. Reflective device 114 functions in a manner similar to light emitter 14 described above, however it does not emit a new beam of radiation but rather reflects the original beam of radiation. It has been found advantageous to use a mirror for reflective device 114. This has the advantage of being biocompatible and inexpensive. Further, it is a relatively efficient device for reflecting radiant energy. The mirror may be any suitable size, however, it has been found preferable to limit the size of the mirror in length and width to from about 0.02 mm to about 5 mm for this application, making the mirror invisible to the patient in which it is implanted. It will be readily apparent to those skilled in the art, that multiple mirrors may be implanted simultaneously in any number of locations on the intraocular lens system.

When measuring a substance by using conventional laser light, the absorption of a specific wavelength is measured. As stated above, each substance in the body absorbs a specific wavelength of light. By using a spectroscope as receiver system 118, virtually any chemical can be measured in the body, as long as the specific wavelength that the substance absorbs is known. The substance will absorb the light that is reflected out of the eye and the spectroscope will filter the information and analyze the substance, thus measuring the amount of the substance in the body. Measurement using a spectroscope is generally preferred in that it allows the user to employ the same source of conventional laser light to measure many different chemicals and compositions.

When a specific wavelength is projected by a AOTF, it is possible to detect the beam of radiation using a detector 124 advantageously comprising a polarizing crystal similar to that used in radiant energy source 112, however, any suitable detector may be used.

Additionally, it is possible to combine reflective device 114 with a repolarizing device 115 that will repolarize the light reflected off of the reflective device to the light's polarization prior to contacting the mirror. When using polarized light to measure the amount of a substance in the body, the number of degrees in which the polarized light shifts is directly related to the amount of substance in the body. Certain substances, preferably, glucose can be measured in this manner. The polarized light is also shifted when it is reflected off of the mirror. It is preferable to measure only the shift as the light passes through the eye, which results in a more accurate measurement. This device 115 will change the direction of the polarization to the direction it was before it contacted the mirror, thus making the shift in polarization only due to the amount of the substance in the eye resulting in a highly accurate measurement.

In operation, radiation source 112, such as described above, is positioned to project a beam of radiation 120 into a portion of the eye 28 of a patient at a location for which the presentation or concentration of a particular substance or compound is to be determined. Reflective device 114, attached to intraocular lens system 52, which is implanted in the eye 28 of a patient, is positioned to reflect outwardly the radiation 120. Detector 24, in turn, is positioned to detect the reflected radiation 122. The detected signal is processed by processor 26 to determine the absorption and/or polarization shift of each wavelength of radiation in the detected signal. This information may then be displayed or further processed to generate information for a doctor or other medical care provider regarding the biomedical condition for which the test is being administered.

By attaching a mirror to an intraocular lens system as described, the intraocular lens may be manufactured with a mirror coupled to the surface or embedded under the surface prior to insertion in the eye. This procedure may reduce cost and may reduce the number of procedures a patient must undergo.

The features of diagnostic system 100, which are similar to diagnostic systems 10 and 50, are identified with like reference numbers. The same description of those similar features is applicable.

While a few specific embodiments have been chosen to illustrate the invention, it will be understood by those skilled in the art that various changes and modifications can be made therein without departing from the scope of the invention as defined in the appended claims.

What is claimed is:

1. A system for testing for the existence of a biomedical condition using radiant energy, comprising:

a radiant energy source for projecting radiation into and through the tissue of a portion of an animal test subject;

a light emitter sized and configured for implantation in the body of the animal test subject for emitting a known wavelength of light through the body when activated by said projected radiation of said radiant energy source;

a receiver including a detector positionable relative to said light emitter for detecting said known wavelength of light emitted therefrom; and a processor in communication with said detector for calculating changes in said known wavelength of light after passage through the body of the animal test subject to determine the existence of a biomedical condition.

2. A system for testing according to claim 1, wherein said light emitter is a vertical-cavity surface-emitting laser.

3. A system for testing according to claim 1, further comprising a plurality of light emitters.

4. A system for testing according to claim 3, wherein each of said plurality of light emitters is a vertical-cavity surface-emitting laser.

5. A system for testing according to claim 1, wherein said projected radiation is selected from the group consisting of visible light and infrared light.

6. A system for testing according to claim 1, wherein said light emitter is sized and configured for implantation in an eye of the test animal.

7. A system for testing according to claim 6, wherein said light emitter is sized and configured for implantation on the iris of the eye.

8. A system for testing according to claim 6, wherein said light emitter is sized and configured for implantation on the corneal stroma of the eye.

9. A system for testing according to claim 1, wherein said processor is a spectroscope that analyzes the modulation of said known wavelength of light.

10. A system for testing for the existence of a biomedical condition using radiant energy, comprising:

an intraocular lens system having a lens portion and haptics sized and configured for implantation in an eye of an animal test subject;

a radiant energy source for projecting radiation into and through the cornea of said eye of said animal test subject;

a light emitter attached to said intraocular lens system for emitting a known wavelength of light through the eye when activated by said projected radiation of said radiant energy source; and a receiver including a detector for detecting said known wavelength of light; and a processor in communication with said detector for calculating changes in said known wavelength of light after passage through the eye of the animal test subject to determine the existence of a biomedical condition.

11. A system for testing according to claim 10, wherein said light emitter is a vertical-cavity surface-emitting laser.

12. A system for testing according to claim 10, further comprising a plurality of light emitters.

13. A system for testing according to claim 12, wherein each of said plurality of light emitters is a vertical-cavity surface-emitting laser.

14. A system for testing according to claim 10, wherein said projected radiation is selected from the group consisting of visible light and infrared light.

15. A system for testing according to claim 10, wherein said light emitter is attached to the surface of said lens portion.

16. A system for testing according to claim 10, wherein said at least one light emitter is embedded in the lens portion.

17. A system for testing according to claim 10, wherein said light emitter is attached to the haptics of the intraocular lens system.

18. A method for determining a biomedical condition of an animal, the steps comprising implanting, within the body of an animal test subject, a light emitter capable of emitting a measuring beam of light of a known wavelength, projecting an activating beam of radiant energy through the body and onto the light emitter, to activate the light emitter and emit the measuring beam, conducting the measuring beam out of the body, detecting the measuring beam of a known wavelength of light, and analyzing a modulation of the measuring beam of the known wavelength of light, thereby determining a biomedical condition in the body.

19. A method for determining a biomedical condition of an animal according to claim 18, wherein the implanting step includes implanting a light emitter that is a vertical-cavity surface-emitting laser.

20. A method for determining a biomedical condition of an animal according to claim 18, further comprising the implanting step includes implanting a plurality of light emitters, wherein said plurality of light emitters are vertical-cavity surface-emitting lasers.

21. A method for determining a biomedical condition of an animal according to claim 18, wherein the activating beam is selected from the group consisting of visible light and infrared light.

22. A method for determining a biomedical condition of an animal according to claim 18, wherein the implanting step includes the step of implanting the light emitter in an eye of the test animal.

23. A system for testing for the existence of a biomedical condition using radiant energy, comprising:

an intraocular lens system having a lens portion and haptics sized and configured for implantation in an eye of an animal test subject;

a radiant energy source for projecting radiation into and through the cornea of the eye of the animal test subject;

a reflective device attached to said intraocular lens system for reflecting said radiation out of the eye;

a receiver including a detector for detecting said reflected radiation; and a processor in communication with said detector for calculating changes in said reflected radiation after passage through the body of the animal test subject to determine the existence of a biomedical condition.

24. A system for testing according to claim 23, wherein said reflective device is at least one mirror.

25. A system for testing according to claim 24, wherein said mirror is coupled to the surface of said lens portion.

26. A system for testing according to claim 24, wherein said mirror is embedded in the lens portion.

27. A system for testing according to claim 24, wherein said mirror is coupled to the haptics of the intraocular lens system.

28. A system for testing according to claim 23, further comprising a plurality of reflective devices, wherein said plurality of reflective devices are a plurality of mirrors coupled to said intraocular lens system for reflecting radiation out of the eye.

29. A system for testing according to claim 28, wherein said plurality of mirrors are coupled to the surface of said lens portion.

30. A system for testing according to claim 28, wherein said plurality of mirrors are embedded in the lens portion.

31. A system for testing according to claim 28, wherein said plurality of mirrors are coupled to the haptics of the intraocular lens system.

32. A system for testing according to claim 23, wherein said radiant energy source is polarized.

33. A system for testing according to claim 32, wherein said reflective device is combined with a device that repolarizes the radiant energy after the radiant energy is reflected off said reflective device.

* * * * *